United States Patent
Tyler et al.

(10) Patent No.: US 9,775,512 B1
(45) Date of Patent: Oct. 3, 2017

(54) BINOCULAR EYE TRACKING FROM VIDEO FRAME SEQUENCES

(71) Applicants: Christopher W. Tyler, San Francisco, CA (US); Spero C. Nicholas, San Francisco, CA (US); Lora T. Likova, Greenbrae, CA (US)

(72) Inventors: Christopher W. Tyler, San Francisco, CA (US); Spero C. Nicholas, San Francisco, CA (US); Lora T. Likova, Greenbrae, CA (US)

( * ) Notice: Subject to any disclaimer, the term of this patent is extended or adjusted under 35 U.S.C. 154(b) by 0 days.

(21) Appl. No.: 14/663,417

(22) Filed: Mar. 19, 2015

Related U.S. Application Data

(60) Provisional application No. 61/955,445, filed on Mar. 19, 2014.

(51) Int. Cl.
| | |
|---|---|
| *A61B 3/113* | (2006.01) |
| *A61B 3/14* | (2006.01) |
| *A61B 3/00* | (2006.01) |
| *G06F 3/01* | (2006.01) |

(52) U.S. Cl.
CPC ............ *A61B 3/113* (2013.01); *A61B 3/0025* (2013.01); *A61B 3/145* (2013.01); *G06F 3/013* (2013.01)

(58) Field of Classification Search
CPC ....... A61B 3/113; A61B 3/145; A61B 3/0025; A61B 3/14; A61B 3/103; A61B 3/1208; A61B 3/1225; A61B 1/1015; G06K 9/00597; G06K 9/00228; G06F 3/013; G06T 2207/10016
USPC ....... 351/210, 205, 206, 209, 220, 221, 246; 382/103, 117, 118
See application file for complete search history.

(56) References Cited

U.S. PATENT DOCUMENTS

| | | | | |
|---|---|---|---|---|
| 4,973,149 A | * | 11/1990 | Hutchinson | A61B 3/113 351/210 |
| 2005/0175218 A1 | * | 8/2005 | Vertegaal | A61B 3/113 382/103 |
| 2009/0201309 A1 | * | 8/2009 | Demos | G01J 3/02 345/589 |

FOREIGN PATENT DOCUMENTS

| | | | | |
|---|---|---|---|---|
| DE | 19719695 | * | 11/1998 | A61B 5/16 |

OTHER PUBLICATIONS

English translation od DE 19719695, machine translated May 2016.*

* cited by examiner

*Primary Examiner* — Jie Lei
(74) *Attorney, Agent, or Firm* — Howard Cohen

(57) ABSTRACT

A system for tracking the 3D position and gaze angles of the eyes over their full range of movement in space relative to a camera or relative to the head without the need for calibration or specialized image aquisition equipment. The eyes are tracked on the basis of surface features in relation to a geometrical 3D model of the eyes by means of a standard consumer device for recording the sequence of face images in conjunction with computing capability. The resultant eye positions and pupil diameters are used to control the information on a viewing screen or in another device. The system further allows for deriving the angular trajectories of the eye movements and for fitting model functions of these trajectories to characterize the degree of normality and deviation from normality of the binocular eye movement parameters.

19 Claims, 7 Drawing Sheets

BINOCULAR EYE TRACKING FROM VIDEO FRAME SEQUENCES

CROSS-REFERENCE TO RELATED APPLICATION

This application claims the priority date benefit of U.S. Provisional Application 61/955,445, filed Mar. 19, 2014.

FEDERALLY SPONSORED RESEARCH

Not applicable.

PARTIES TO A JOINT RESEARCH AGREEMENT

Not applicable.

SEQUENCE LISTING, ETC. ON CD

Not Applicable.

PRIOR DISCLOSURES

Not Applicable.

BACKGROUND OF THE INVENTION

Field of the Invention

This invention relates to methods and apparatus for the measurement of human eye movements.

Description of Related Art

The measurement of human eye movements is important for the assessment of damage to the eyes, optic pathways, and brain mechanisms controlling oculomotor behavior. The eyes see clearly in only one central region, so it is necessary for the eyes to direct their gaze directly on any target object of interest in order to see it clearly. In order to look directly at any target, the eyeballs must rotate or move in their sockets so that light from the target is centered on the central region or fovea of the retina. The efficiency of such eye rotations or movements is called oculomotor performance and, for accurate binocular vision in 3D space, the two eyes need to be coordinated to target or look at the same object of interest simultaneously in both eyes, with both lenses focusing on the target. Moreover, effective vision requires the pupil to adjust the light level reaching the retinas for an optimal match to the dynamic range of the retina's photoreceptors. Such coordinated targeting, lens focusing, and light-level adjustment is called binocular coordination and is a primary function of the visual process that is necessary for effective vision.

One valuable use for eye movement measurement is for the diagnosis of brain damage and drug toxicity, which produce a characteristic slowing of eye movement dynamics. Also, another important reason for measuring binocular eye movements is in the diagnosis of strabismus conditions, in which one eye deviates from the target or gaze angle of the other eye, indicating a loss of binocular coordination that requires medical treatment. There are many forms of strabismus with diverse causes that are difficult to distinguish, making the ability to quantify the dynamics of binocular eye movements an important diagnostic tool.

Many systems have been patented for both head-mounted and remote camera eye tracking, typically from one, or both, of two kinds of infrared signals from an eye: corneal reflections and pupil images. These include U.S. Pat. No. 4,973,149 to Hutchinson (1990), U.S. Pat. No. 5,325,133 to Luo (1994), U.S. Pat. No. 5,668,622 to Charbonnier and Masse (1997), U.S. Pat. No. 5,912,721 to Fukui, Okamoto, and Yamaguchi (1997) and the Google Glass monocular eye tracking system described in U.S. Pat. No. 8,398,239 to Horning, Ohnstein, and Fritz (2013).

U.S. Pat. No. 6,568,809 to Trajkovic, Gutta, and Colmenarez (2003) describes a device for automatic adjustment of a zoom lens that incorporates a binocular gaze tracking system but only refers to gaze tracking capabilities that are "known in the art", without providing any specifics.

U.S. Pat. No. 6,926,429 to Barlow, Harter, Scharenbroch, and Newman (2005) and a paper by Bretzner and Krantz ("Towards low-cost systems for measuring visual cues of driver fatigue and inattention in automotive applications", Proceedings of the IEEE International Conference on Vehicular Electronics and Safety. 2005, pp. 161-164, 2005) describe monocular eye tracking by means of infrared imaging systems using the iris-corneal boundary (limbus) as the indicator of eye position.

Despite their different methodologies, all these systems require external apparatus close to the eyes, some mounted on the head by means of a spectacle frame, goggles or a headband of some kind, others mounted on the table in front of the viewer, and all require calibration procedures.

Recent publications have described eye-tracking of the iris from video sequences based on pattern recognition of the configuration of features in the eye region of the face with an artificial neural network in a series of calibrated eye fixation positions (Baluja and Pomerleau, "Non-intrusive gaze tracking using artificial neural networks." Research Paper CMU-CS-94-102, School of Computer Science, Carnegie Mellon University, Pittsburgh Pa., USA, 1994; Holland and Komogortsev, "Eye tracking on unmodified common tablets: Challenges and solutions." ACM Symposium on Eye Tracking Research & Applications (ETRA 2012), 2012). The latter authors developed this system for tablet computer applications, indicating the broad promise of device-free eye-position tracking capability. Their system had a sampling rate of about 1 frame every 5 seconds, which is sufficient for monitoring eye position at a slow rate, but entirely insufficient for the assessment of oculomotor dynamics requiring frame rates of 30 per second or higher.

A paper by Nagamatsu, Iwamoto, Sugano, Kamahara, Tanaka, and Yamamoto, "Gaze estimation method involving corneal reflection-based modeling of the eye as a general surface of revolution about the optical axis of the eye." Institute of Electronics, Information and Communication Engineers Transactions, 95-D(6):1656-1667, 2012, describes a video-based gaze estimation system incorporating a 3D model of the eyeballs and irises. They do not include the eyelids or the pupils as components of their model. Their system uses two infrared cameras is designed to estimate gaze angles by averaging over a minimum of 30 frames, and is therefore not suitable for tracking rapid eye movements.

A key issue both for understanding the focus of interest of a person and for diagnosing any deficiencies in their oculomotor capabilities is the capability of tracking the positions of the eyes. Although this capability may be achieved by a variety of specialized equipment, such as infrared pupil trackers mounted on glasses or goggles, such equipment constrains the person's activities in various ways, and may interfere with the procedures of an eye care professional assessing deficiencies of their oculomotor capabilities. Heretofore in order to assess the positions of both eyes through the use of images captured by a distant video camera trained on the face, it was necessary to use specialized eye-tracking equipment, and this had to be calibrated with a series of eye fixations on targets in known positions in space.

Most previous approaches to the capability of tracking gaze angles from a video frame have the one or several of the following limitations:

a) They measure the movements of one eye only.
b) They require prior calibration of the relationship of the configurations of image features to the eye rotation vectors.
c) They do not provide the ability to track to the extreme eye positions needed for quantifying ophthalmic and optometric evaluations of oculomotor control.
d) They are subject to errors in the eye movement estimation due to interference from concurrent head movements
e) They do not provide analysis of the ocular dynamics of the eye rotation.

As a consequence of these shortcomings, the state of the art in video gaze tracking was recently characterized by Hansen and Ji ("In the eye of the beholder: a survey of models for eyes and gaze." IEEE Transactions on Pattern Analysis and Machine Intelligence. 32, 478-500, 2010) with the following statement: "Another future direction will be to develop methods that do not require any calibration. This does not seem to be possible given the current eye and gaze models."

BRIEF SUMMARY OF THE INVENTION

The present concept is focused on eye tracking free of any specialized eye-tracking devices other than an unmodified video camera directed toward the face. In this sense, the approach may be called 'device-free eye-tracking', based solely on the video sequences available for download from the internet or from general-purpose video recording devices, playable on general-purpose video playback devices such as personal computers.

The eye-tracking system is based on a Bayesian 3D model of the configurations of the eyeballs, irises, pupils, axis geometries, and eyelids of the two eyes. The term "Bayesian" is used to imply that the model incorporates parameter values from prior knowledge of the known configurations of human eyes. The Bayesian 3D model is used to derive to the configuration of the features of the eyes for application to any video file of sufficient resolution. The video file of a person's face is fed into an analysis system to compare the information in each video frame with the 2D image of the eye region of the model face generated from a projected view of the 3D model of this region. The colors in this projected 2D image are progressively optimized for best fit to the in each video frame of the video file by adjusting the parameters of the 3D model to provide estimates of the angle of gaze, eyelid aperture, and pupil diameter of each eye in each video frame. These estimates are then used to generate an output consisting of the gaze trajectories and pupil diameter variations of the two eyes over time (or single eye, if only one eye is visible in the video image). In many applications, it is desirable to provide dynamic analysis of these time functions to characterize their degree of normality. To do so, the gaze trajectories and pupil diameter variations are fitted with model mathematical functions to determine the kinetic and dynamic parameters that characterize their time functions.

The system is designed for operation in the medical fields of ophthalmology, optometry, neurology, psychiatry, and sports medicine, particularly as applicable to traumatic injury to the eyes and brain and to the debilitative diseases of aging of the oculomotor control systems. It is also applicable to the assessment of the gaze angle and focus of attention of computer users from computer-mounted cameras.

Advantageous Effects

In one or more aspects, the approach of fitting the 3D model of the eyes is advantageous over previous systems for the following reasons:

a) By analyzing the positions of both eyes in each video frame, the system can allow assessment of the combined 3D system of the two eyes together, providing the capability of diagnosing deficiencies of the oculomotor capabilities that fall under the clinical definition of strabismus.
b) By fitting the features of the 3D model to the corresponding image features in the video frame, the system can determine the positions of both eyes from a single video image.
c) By incorporating known average values for the geometric features of the eyes in the normal population, the system can avoid the need for calibration, and can be used with videos from any source without the need to specify their recording conditions.
d) By the use of the 3D model of the two eyes, the system can avoid distortions in the estimated angles of gaze as the eyes approach extreme rotation angles.
e) Because the system is based on of fitting a 3D model, it can estimate the changes in the posture of the head over time and specify the eye positions relative to the head position, which is a critical requirement for ophthalmic assessment of disorders of eye control such as strabismus, nystagmus, and ocular instability.
f) When used for ophthalmic evaluations of clinical disorders of eye control, the system can provide accurate assessment of the horizontal, vertical and oblique angles of rotation of the eyes even when parts of the iris and pupil are hidden by the eyelids under the extreme angles of gaze encountered in these clinical disorders.
g) Because estimated gaze angles of the two eyes from each video frame are tracked over time, the system provides enhanced, quantitative diagnosis of ophthalmic disorders such as strabismus, nystagmus and gaze instabilities.

Various other aspects can provide other advantages.

DETAILED DESCRIPTION OF THE INVENTION

Assessment of Binocular Coordination and Oculomotor Dynamics

In a first embodiment of the eye-tracking system, a video file is made of a subject's face in which the eyes are visible to sufficient resolution (of the order of 50 pixels/eye width). This video file is fed into an analysis system that performs a sequence of operations on the information in each video frame to generate an output consisting of the estimated gaze trajectories and pupil diameter variations of the two eyes over time (or single eye, if only one eye is visible). It is desirable to provide dynamic analysis of these time functions to characterize their degree of normality. To do so, the gaze trajectories and pupil diameter variations are fitted with model mathematical functions to determine the kinetic and dynamic parameters that characterize their time functions.

Figure 1:
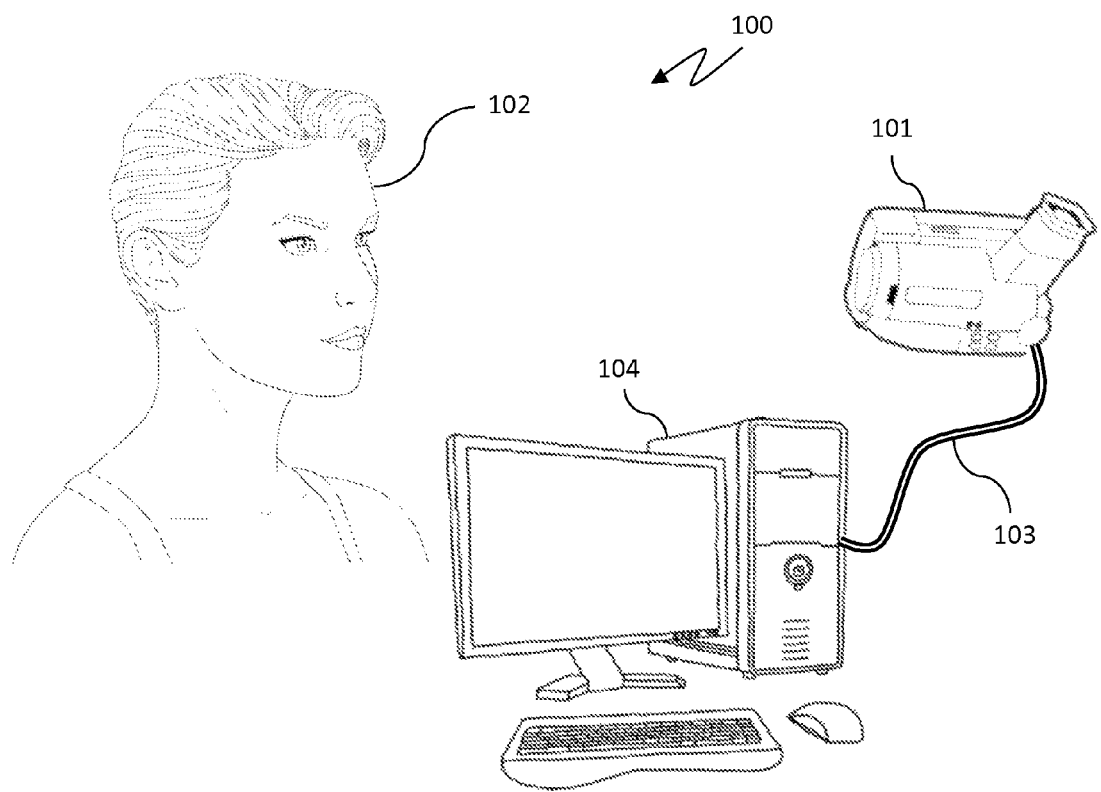
FIG. 1 is a schematic diagram of a system for tracking the position and gaze angle of the eyes relative to the camera in video or other image sequences.
Figure 2:
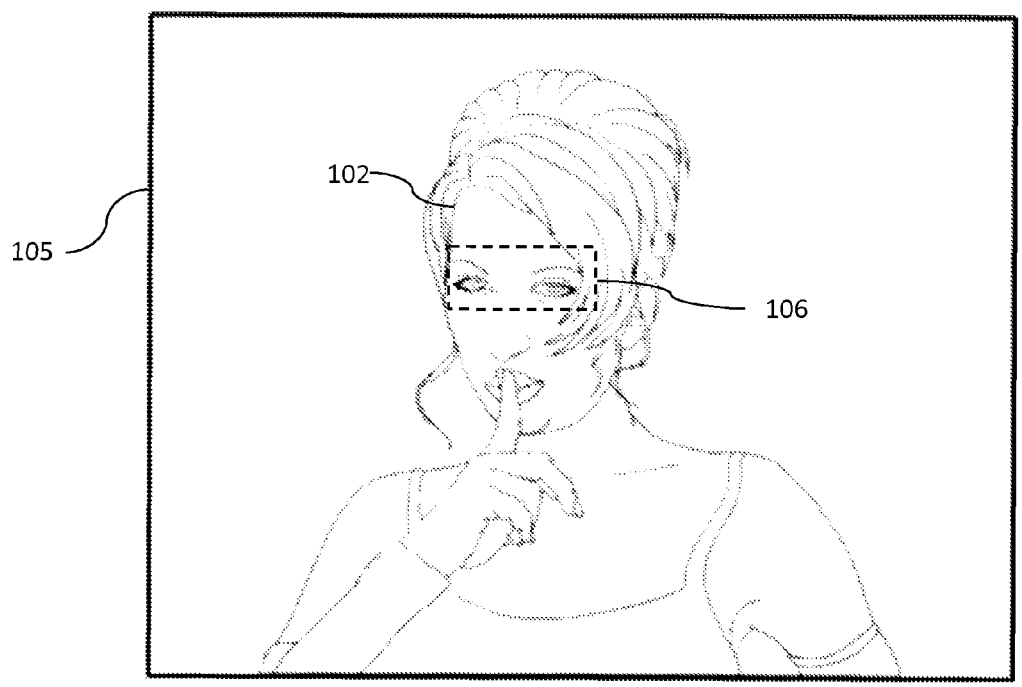
FIG. 2 is an example of a video frame image with the eye region identified for analysis.

FIG. 1 is a schematic diagram of an eye-tracking system 100 consisting of a video camera 101 recording a video sequence of the face of a subject 102 showing the two eyes with an image resolution of 200 pixels across the image of the face. The recording is sent via cable 103 to a computer 104 for the analysis of the eye positions in each video frame. This system will operate with virtually any make or model of video or movie camera. Thus, system 100 constitutes means for obtaining a video image of an eye of a subject and sending this video image to computer 104 for storage FIG. 2 shows a view of the 2D image of a video frame captured by video camera 101 directed towards the face of a subject 102. The eye region of the face used for the analysis of eye position is indicated by dashed rectangle 106.

Figure 3:
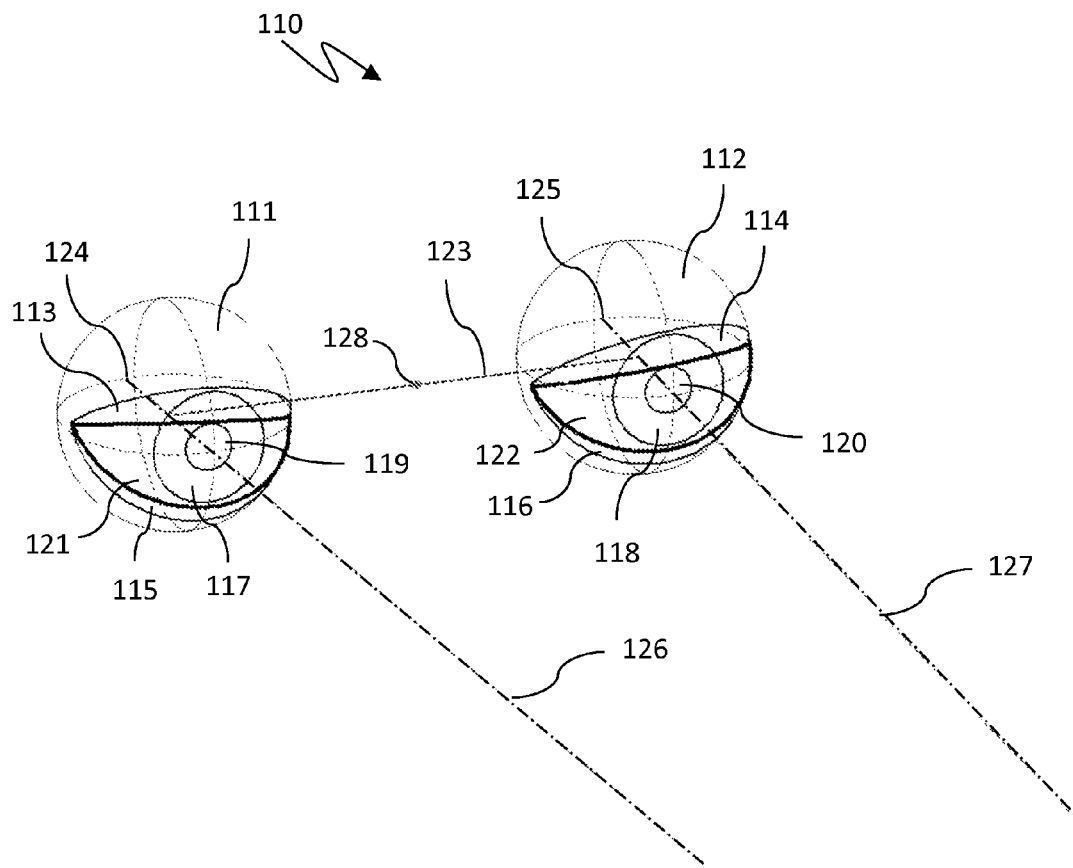
FIG. 3 is a perspective view of a Bayesian 3D geometric model of the eyes and eyelids used to fit the corresponding features of an image in a video frame, with the eyes in primary position.

FIG. 3 shows a perspective view of the geometric elements of a 3D model of two eyes 110 to be fitted to the video image with the eyes in primary position. In one implementation, the 3D model is described as 'Bayesian' because the geometry and dimensions of the fixed elements of this model are specified according to the average geometry of the eyes and face of an age-matched human. It will generally be termed the "3D model." The left and right eyeballs are represented by two spheres 111 and 112 and are overlaid in the front by upper eyelids 113 and 114 and lower eyelids 115 and 116 (shown as transparent for clarity). The eyeballs contain the zones of the circular irises 117 and 118. The inner boundaries of the irises form the zones of the pupils 119 and 120, which are in the same plane as the irises. The zones between the outer boundaries of the irises and the inner boundaries of the eyelids form the exposed regions of the scleras 121 and 122, known as the 'whites of the eyes.' The dashed elliptical construction lines indicate the cardinal planes of the eyeballs. The locations of foveas 124 and 125 at the back of the eyeball are the regions of sharpest vision that are the origins the left and right lines of sight 126 and 127 extend through the centers of the pupils to define the gaze angle of each eye. Line 123 connects the centers of eyeballs and its center point 128 has position (x,y,z) defined in terms of horizontal (x), vertical (y) and distance (z) coordinates with respect to the center of the video camera lens. The orientation of line 123 in 3D space is defined by its azimuth ($\theta_x$) and elevation ($\theta_y$) angles in relation to the horizontal position with the two ends equidistant from the video camera lens.

The 3D model 110 has five fixed parameters and 16 adjustable parameters. The fixed parameters are the diameters of eyeballs 111 and 112, the diameters of irises 117 and 118, and the length of line 123 connecting the eyeballs. The adjustable parameters are the three spatial dimensions of the position of each eyeball 111 and 112, the two dimensions (azimuth and elevation) of the locations of the foveas in the back surfaces of each eye, the diameters of pupils 119 and 120 of each eye, and the angular boundaries of sclera defined by the sector angles of upper eyelids 113 and 114 and lower eyelids 115 and 116. The fixed parameters are set on the basis of any prior information known about the subject 102 of the video. Thus, the 3D geometric model 110 constitutes for providing adjustable parameters of the geometric features of the eye region, including the 3D positions, angles of gaze, and pupil sizes of the eyes relative to the position and size of the head.

Figure 4:
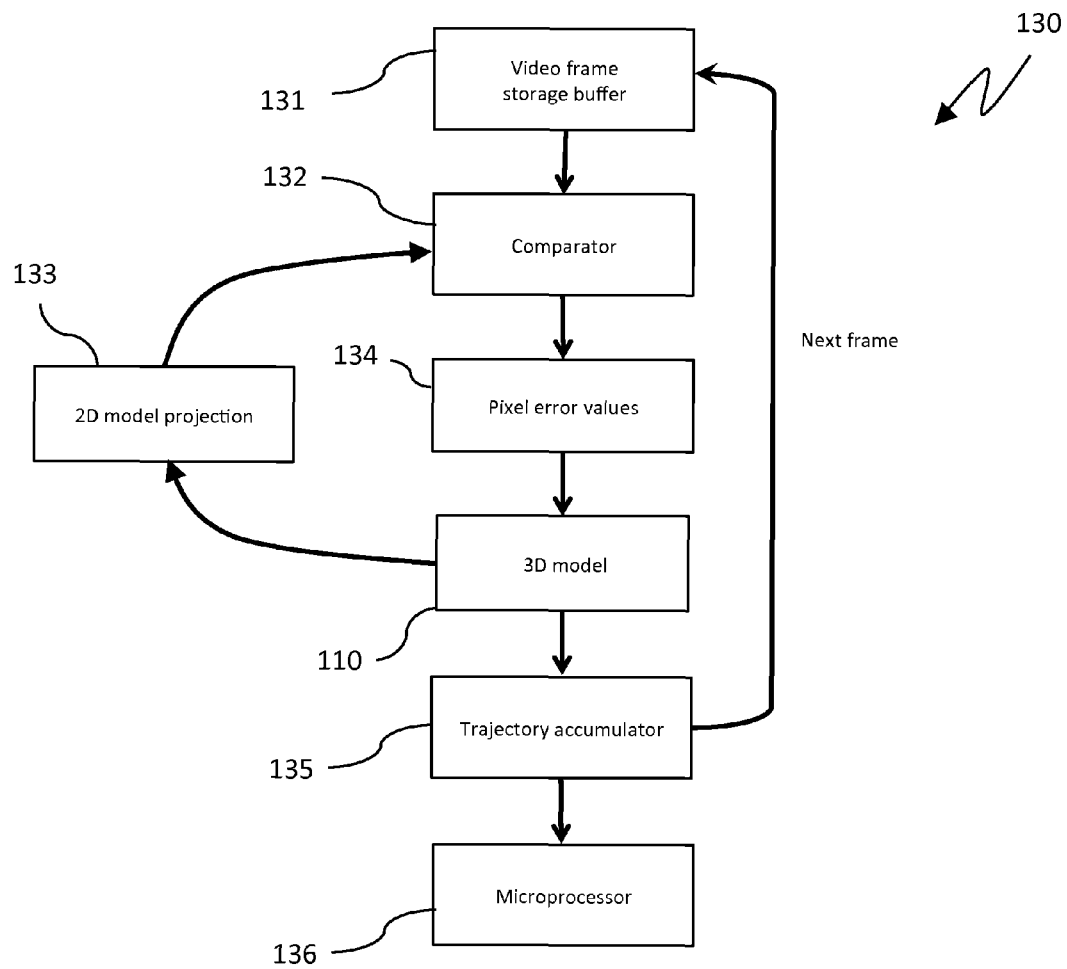
FIG. 4 is a flowchart of a sequence of operations involved in tracking the position and gaze angles of the eyes from video or other image sequences.

FIG. 4 is a flowchart of the stages of processing 130, implemented in computer 104 of FIG. 1. The digital information from one video frame 105 of the eye region of a face 102 from a video camera 101 (FIG. 1) is a 2D representation, which is imported into an electronic storage buffer 131 of computer 104. The computer compares it with a 2D view of the eye-region of the face (106 in FIG. 2) projected from the 3D model 110 (FIG. 3) of the geometric configurations of the two eyes. The projected 2D view of the eye-region is generated at the same pixel resolution as video frame 105. Each of zones 113-122 (FIG. 3) of the projected 2D view of the eye region has designated color initialized from the colors of typical human face; pinkish for the eyelid skin areas 113-116, whitish for scleral regions 121-122 of the eye, brownish for irises 117-118, and blackish for pupils 119-120.

Next, an optimization procedure 132-134 (FIG. 4) is performed for each frame by a series of fitting procedures to obtain an optimal fit of the pixels in the projected 2D view from the 3D binocular model to the corresponding pixels in the eye region of the face in the video frame. Steps 132-134 consists of the following sub-steps:

a) The information from video frame 105 is sent to storage buffer 131.

b) The 3D model of the geometric configurations of the two eyes 110 is initialized with typical values of the anatomy of the human face and adjustable parameters.

c) The 3D model geometry 110 is conveyed to a 2D projection (block 133) of the eye region 106 of the human face (FIG. 2) to define the boundaries of the ocular features 113-122 (FIG. 3), and is initialized with color assignments from a typical video frame. Thus, sub-step (c) constitutes means for deriving a projected 2D view of the 3D geometric model of the eye region of the face and means for defining a plurality of zones of this projected 2D view of the eye region.

d) The trichromatic red, green, and blue color values of each pixel within each zone 113-122 of the projected 2D view 133 are compared in comparator 132 with those for each corresponding pixel in video frame 105 to generate pixel error values (block 134) for the pixels in each zone 113-122. Thus, sub-step (d) constitutes means for comparing the trichromatic values of a plurality of pixels within each zone of the projected 2D view of the subject's face with those of each corresponding pixel in the video image to define a trichromatic error value for each pixel. The term "trichromatic" is intended to include situations in which only part of the trichromatic color space is employed, such as restriction to a monochromatic grayscale axis of the trichromatic color space, or any other partial combination of the trichromatic color values of a pixel.

e) The pixel error values in each zone 113-122 are combined to provide a combined error value over a plurality of pixels in each of the image zones constrained by the 3D model 110. Thus, sub-step (e) constitutes means for combining the trichromatic pixel error values in each zone to provide a combined error value over a plurality of image zones constrained by the 3D geometric model 110.

f) The adjustable parameters of the 3D model 110 are then varied in an iterative loop by a multidimensional search function to determine the values for which the combined error across all zones converges on a minimum value to represent the best fit of the 3D model 110 for this video frame. Programs or subroutines for fitting a mathematical function for such fitting to a set of data values are known and available for purchase, e.g., from The Mathworks, Natick, Mass. Thus, sub-step (f) constitutes means for varying the adjustable parameters of the geometric 3D model in an iterative loop 132-134 until the combined pixel error across said plurality of image zones converges to a minimum value.

The values of the adjustable parameters of 3D model 110 specified in [0032] are then passed to a trajectory accumulator 135 that stores them as the values for the eye positions in the initial frame. The accumulator then triggers the system to input the next video frame in storage buffer 131 into comparator 132 and activates the fitting procedures for the eye region in this second frame to generate the best-fitting adjustable model parameters. The optimized values for these adjustable parameters of 3D model 110 are then passed to a trajectory accumulator 135, which stores them as the second value of the gaze trajectories of the two eyes.

This process is iterated for each video frame 105 (or of a subsampled plurality of frames sufficient for the particular diagnostic or analytic application) until the set of values derived for the variation of each adjustable parameter over the video frames are accumulated in trajectory accumulator 135 to form the full set of values to specify the gaze trajectories over time. The change in the position and rotational values of the eyeball over time can be calibrated by specifying the time of occurrence of of each frame. The trajectory analysis also includes the size of the pupil apertures and the aperture angles of the eyelids over time. Specifically, the gaze position, pupil size and eyelid aperture of one eye is defined as the set of optimized adjustable parameter values for each frame:

Horiz Position (mm)
Vert Position (mm)
Face Distance (mm)
Foveal Azimuth (deg)
Foveal Elevation (deg)
Pupil Diameter (mm)
Upper Eyelid Angle (deg)
Lower Eyelid Angle (deg)

The full binocular gaze trajectory is defined as the matrix of these parameters over a sequence of frames, together with the time of occurrence of each analyzed frame.

At a final processing stage, microprocessor 136 performs a quantitative analysis of the adjustable parameters of the gaze, pupil size and eyelid aperture trajectories following a given type of eye movement in response to a predetermined visual target movement, such as a step change in position.

Figure 5:
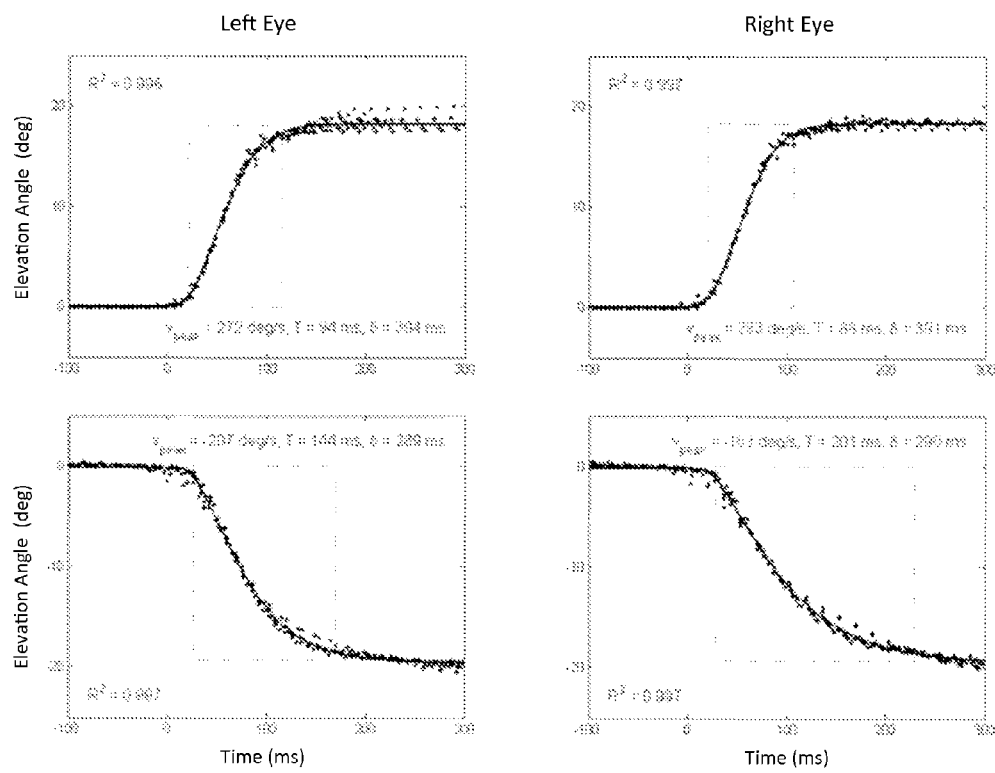
FIG. 5 is an example of four types of eye movement data illustrating the fitting of dynamic model functions to the data from a series of upward and downward saccadic jumps.

The mathematical analysis of each trajectory consists of the optimized fits of a model mathematical function to the trajectories to characterize the eye movement dynamics of the two eyes (see examples in FIG. 5). The preferred mathematical function used for this purpose in FIG. 5 is the integral of a delayed multipole filter function f(t) of the form $$f(t) = a \cdot \int_\Delta^t [(t'-\Delta)^{\alpha-1} \cdot e^{-(t'-\Delta)/\beta}] dt' + b \qquad (\text{eq. 1})$$

The parameters of the multipole filter function of time (t), assuming e as the natural logarithm base, are as follows:

α—multipole order of the filter function
β—time constant of the filter function
Δ—onset delay of the filter function relative to the stimulus event.
a—amplitude scaling parameter
b—zero offset parameter The five-parameter model function fits for the movement dynamics of each eye during a given eye movement provide a means of comparing a diagnosis of abnormalities in eye movement dynamics relative to a normative database of healthy oculomotor dynamics. Thus, trajectory accumulator 135 provides the means for storing the values of said adjustable parameters, including the 3D positions, angles of gaze, and pupil sizes of said eyes, under conditions providing the minimum value of the combined pixel error.

A typical form of eye movement trajectory is the trajectory produced by the rapid jumps of the eye, known as saccades, following a stimulus event. An example that illustrates the fitting of dynamic model functions to the eye movement data is shown in FIG. 5 for vertical saccades. These particular eye movements were chosen to show the kind of normal variation that occurs in the fitting parameters. The four panels show upward and downward movements of the left and right eyes. Each panel shows sample points for twelve repeated movements overlaid relative to their initiation point. The sample points have been smoothed with a 5-point moving average.

The values of these parameters (α, β, Δ, a, b from eq. 1) are optimized for best fit of the multipole filter function to each of the 16 parameters of the gaze trajectories and eye features of the upper and lower lids and pupil diameters (illustrated as geometric features 111 through 122 in FIG. 2). The optimized values of the fitted functions are then used to derive the response parameters (T, Δ, and $V_{peak}$) listed in each panel of the example calculations of FIG. 5, as follows: the duration T of each eye movement is defined as the elapsed time from 5% to 95% of the total amplitude of the fitted function f(t). The onset delay Δ is the time from a stimulus event to fitted response onset (from eq 1). $V_{peak}$ is the peak velocity of the fitted function f(t). Thus, the procedures of the present and preceding paragraph, which are implemented as a subroutine in the computer program that analyzes the trajectory data, provide means for analyzing the output parameters of the angles of eye gaze and pupil size to derive the kinetic parameters of their dynamic behavior or are fitted by dynamic model functions to characterize their dynamic behavior as a function of time.

For use in the estimation of the coordination of the movements of the two eyes within the head, or the proper estimation of the movement dynamics of each eye, it is necessary to take account of the movements of the head in the video frame 105. The pose of the head is represented by the location of imaginary line 123 joining the centers of two eyeballs in FIG. 3. The center point of line 123 is represented by three location parameters (x,y,z) which represents its position relative to the center of the videocamera lens, and the spatial orientation of line 123 is represented by two parameters of rotation around the x and y axes ($\theta_x$, $\theta_y$). To account for movements of the head, the fits of the adjustable parameters of the 3D model allow the system to derive both the 3D rotation vector of each eyeball and the six parameters of 3D position and rotation specifying the pose of the head. The movements of the head may then be subtracted from the eye movements to provide an uncontaminated estimate of the relative movements of the eyes within the head, which are often the primary focus of clinical diagnostic applications. Thus, changes in 3D position of the head are estimated from parameters defining said geometric 3D model of the two eyes.

Figure 6:
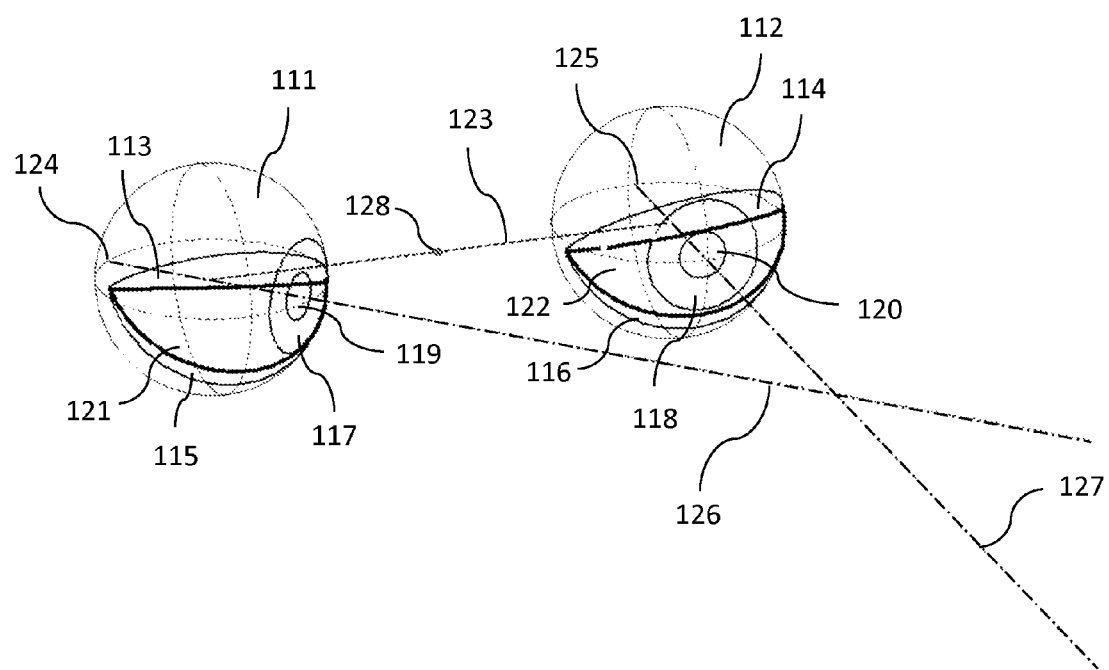
FIG. 6 is a perspective view of a geometric 3D model of the eyes and eyelids used to fit the corresponding features of an image in a video frame, with the right eye rotated inward.

A key advantage and utility of the system is to be able to quantify both the ocular geometry and the dynamic behavior of individuals with strabismus, an ophthalmic condition of chronically crossed eyes or related disturbances of binocular coordination (i.e., abnormal dynamics of the changes in eye position over time). FIG. 6 shows a perspective view of the geometric elements of the binocular model of FIG. 3, but with the right eye rotated inwardly to a crossed-eye angle to illustrate an example of a model fit that would be obtained in a patient with strabismus. This is the final state of the fit of 3D model 110 to the eye region 106 of the patient, who is instructed to look with both eyes straight ahead. In this case, the strabismus means that the patient is unable to coordinate binocular fixation straight ahead and the right eye is crossed to the patient's left side.

As in FIG. 3, spheres 111 and 112 represent the left and right eyeballs showing the upper eyelids 113 and 114, lower eyelids 115 and 116, irises 117 and 118, pupils 119 and 120, and scleras 121 and 122. Dashed elliptical construction lines indicate the cardinal planes of the eyeballs, and the line connecting the centers of eyeballs 123. Left and right lines of sight 126 and 127 extend through the centers of the pupils from the locations of foveas 124 and 125 at the back of the eyeball.

The capability of fitting 3D model to the binocular configuration of the eyes independent of movements of the head allows accurate quantification, under the conditions of an ophthalmic examination from a video taken in the ophthalmologist's office, of both the ocular geometry and the dynamics of the eye movements of patients with binocular coordination problems. These are diagnostic estimates that are available in present ophthalmic practice only by subjective clinical assessment. Thus, their quantification can provide both rigorous, objective documentation and more accurate diagnostic information about the strabismic condition and the effects of any treatment of the condition. These data are valuable for the diagnosis of the success of operations for the correction of strabismic eye misalignment, where uncalibrated image processing approaches without prior knowledge of human ocular geometry are likely to fail.

A further advantage of the system in ophthalmic practice is to incorporate the position of the head in the diagnostic regimen. Many strabismic conditions result in the patient adopting a particular pose of the head in order to achieve the optimal vision with the eyes, or, conversely, cause oculomotor symptoms as a result of orthopedic disorders involving the head position. The system will allow joint quantification of the head position and eye positions in such cases, providing documentation and quantification of both factors. It will also provide information of the joint dynamics of head and eye movements for use in the diagnosis of relevant movement disorders.

Video frame 105 (FIG. 2), and the sequence of such video frames analyzed in flowchart 130, may be derived from other recording systems, such as film sequences from a film camera pointed at the face, digital image sequences from a visible light camera pointed at the face, and digital image sequences from an infrared light camera pointed at the face.

In certain situations it is advantageous to fit 3D model 110 to a single eye of the video frame image, or to the two eyes separately. These situations arise if only one eye is visible in a video frame, or if there are medical reasons to suspect differences in geometry between the two eyes. In this case 3D model 110 may be restricted to the structure of a single eye and fitted with the same sequence of procedures on the reduced set of parameters available for that eye alone.

Figure 7:
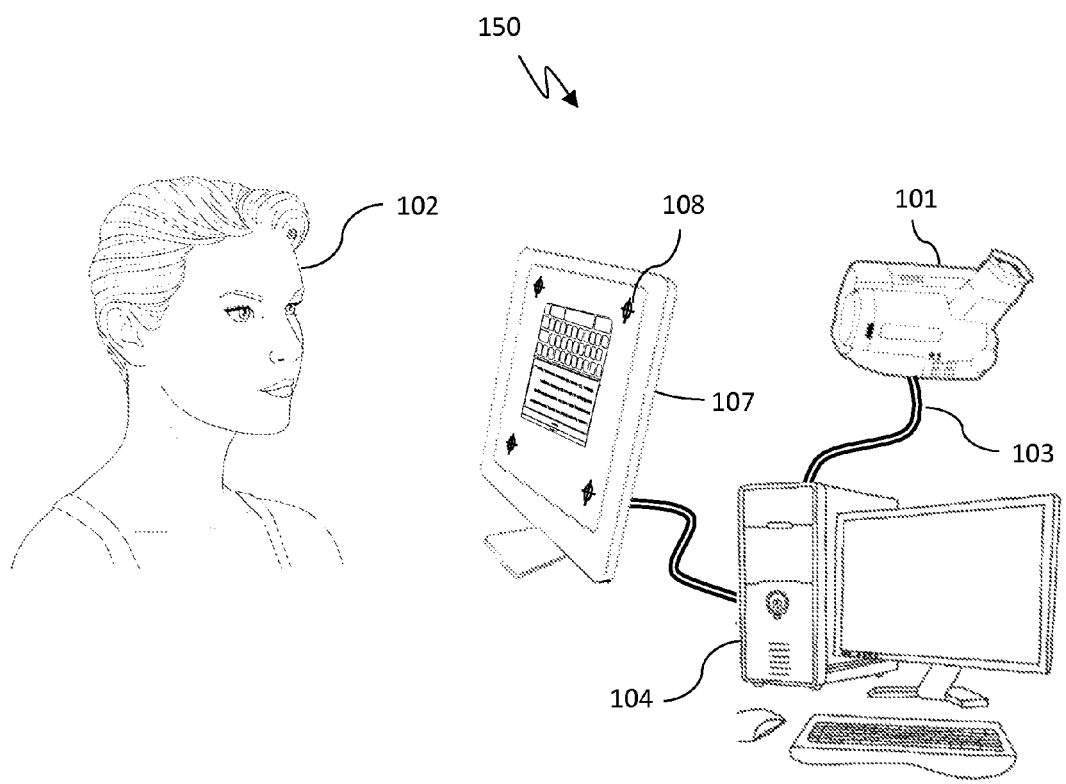
FIG. 7 is a schematic diagram of an eye-tracking system for identifying fixation positions.

In a further embodiment, the eye-tracking system is used for assessing the fixation position of the user on a computer screen containing information of interest to the user, for use in interactive control of screen content by eye movements alone. The fixation position is given by the intersection of the estimated lines of sight (126, 127 in FIG. 3) of the fitted 3D model with the position of the plane of the screen (107 in FIG. 7), which has a known fixed relationship to the position of video camera 101 that provides a view of the eye region of a user's face 102. For this application, no compensation for variation in head position is necessary or desirable. The key parameter is the direct estimate of the intersection of the line of sight with the plane of computer screen 107 (FIG. 7). The control functions of this fixation assessment are the use of the dwell time of the fixation on particular elements of a graphical object on screen 107, and of estimated blinks, both defined by the fit of the 3D model to the features of the irises and eyelids as control events for computer functions. Note that such blink control features are currently used by systems such as the Google Glass monocular eye tracking system (described in the patent to Horning, et al., supra).

FIG. 7 depicts a system for assessment of fixation position of the eyes. The reflection of the incident illumination across the surfaces of irises 117-118 and scleras 121-122 in FIG. 2 is not uniform, and the system incorporates two features that correct for this non-uniformity. One common feature of eye images is the specular reflection of a focal or structured light source illuminating the eyes, which is usually termed the corneal reflex or 'glint'. The approximately spherical nature of eyeballs (111 and 112 in FIG. 3), lubricated by its liquid tear film, means that the specular reflection of a focal light source tends to be compressed into a small bright region that has the potential to disrupt the 3D model fits to the outer and inner boundaries of iris regions.

To minimize such disruption, the fitting procedures 132-134 (FIG. 4) incorporate a process of histogram trimming based on analysis of the pixel frequency distribution of light intensity levels within iris region 117-118 each eye (i.e., the region enclosed by eyelids 113-116). This histogram trimming process uses a threshold frequency criterion to exclude uncommon light intensity levels from the analysis. For example, if the pixel frequency histogram is set to have 64 intensity levels for each of the three trichromatic (red, green and blue: RGB) values of each pixel, the trimming process excludes from the analysis pixels at any RGB intensity level that contain fewer than 5% of the pixels within the iris region. This criterion is chosen is because the area of the focal reflection is typically only about 5% of the area of the target region, and thus cannot contribute more than 5% of its luminance levels. This example illustrates the general principle of histogram trimming; the trimming percentage is an adjustable value determined by the experience with the use of system. In this way, the outlier values of RGB intensity distributions of the trichromatic values of the pixels within the scleral and iris regions are trimmed in order to minimize distortions in the fitting procedures due to specular reflections of incident light sources.

The second form of correction for light intensity variation is to incorporate into 3D model 110 in FIG. 3 the effective shading across the eyeball due to light occlusion by the nose and eyelid structures of the face recorded in the video (region 106 in FIG. 2). Notwithstanding the specular reflection component of the previous paragraph, in most situations there is some level of background illumination impinging on the eyes from all directions, e.g., from the ceiling and walls of a room or from the sky outside. This diffuse illumination component has the property of giving higher reflected light intensity to the more exposed regions of each eye and lower light intensity to the more recessed regions, and those closer to the nose. Incorporating an average model of the effects of face and eye structures 106 on the level of diffuse illumination across the eyes provides the means to identify the ocular features with greater accuracy.

The fitting procedures for correction of light intensity variation consist of the following steps:
 a) A 3D model of the average 3D configuration of the eye structures in a human face 102 is defined.
 b) A z-axis scaling factor for the best fit of this average 3D model to the characteristic face of different races of humans is defined.
 c) The strength of the diffuse lighting in terms of the solid angle of the geometric aperture defined by this scaled 3D face model is computed at each point on the eyeball.
 d) The computed strength of the diffuse lighting to determine the degree of illumination of scleras 121-122 and irises 117-118 incorporated in 3D model 110 are stored for use in fitting procedures 133.

An approximation approach to the compensation for light intensity variations across the sclera is to divide the scleral zone into left and right scleral zones on either side of the iris in each eye. This has the further advantage of compensating for a direction component of the incident light in addition to the uniform diffuse component, Thus, rather than fitting the video image to a 2D projection with the same color across these four scleral zones, the system fits it to a 2D projection with a separate color for each of the four scleral zones. By allowing the four scleral subdivisions to have separate colors, the system accommodates the major differences in lighting that are encountered across each eye and between the two eyes.

Although the system is designed to have the capability to operate directly on video frames without the need for calibration, doing so in the 3D model incorporates fixed known values for the sizes of the eyeballs, the sizes of the irises, and the distance between the eyes. However, we recognize that there are natural variations among individuals for these parameters. It is therefore of benefit, in situations where the individual captured in the video is available for direct measurement, to use the values of the parameters of iris size and distance between the eyes measured from direct observation of the individual rather than relying on fixed values derived from the average for the human population. The size of the eyeballs can also be measured by X-rays or by magnetic resonance imaging, if available. By these means, the fixed parameter values in the 3D model may be calibrated from known values to improve the assessment of the adjustable parameters. This modification is particularly relevant in cases of use of the system for ophthalmic and optometric clinical diagnostic purposes, when it may be used with young children whose iris size and distance between the eyes may differ from those of adults.

Particularly for clinical diagnostic purposes, but also for use in computer screen control functions, it can also be of value to improve the accuracy of the system by directly calibrating system 150 in FIG. 7 for the range of gaze angles over which the eye gaze trajectories will be measured. For such a calibration procedure, the system may be configured to allow the user to enter values for a plurality of quantified angles of gaze by the subject of the image. The calibration procedure consists of the following steps:
 a) A sequence of targets 108 with various combinations of known horizontal and vertical gaze angles is presented on display screen 107 in FIG. 7.
 b) Subject 102 is instructed to fixate on each target as it appears.
 c) A video image is recorded using video camera 101 for each fixation.
 d) Each video image is subjected to the analysis procedures 132-134 of FIG. 4.
 e) The estimated horizontal and vertical angles of gaze are multiplied by calibration scaling factors that minimize the difference between the actual and estimated gaze angles across the set of targets.
 f) The calibration scaling factors are stored with the best-fitting parameters of the 3D model 110 in FIG. 4 and used to scale the values passed to the trajectory accumulator 135.

This calibration procedure will allow adjustment of the estimated parameters of the 3D model for optimum fit to the quantified gaze angles. Adjustment of the 3D model parameters in this way for a given subject constitutes a gaze-angle calibrated version of system 150 (FIG. 7) for that subject. This procedure provides an estimation of the absolute position of the head and eyes with respect to a recording system as a means of controlling the computer functions through information on its screen.

One aspect of eye rotation that is not captured by the rotation of the line of sight (lines 126 and 127 in FIG. 2) is the rotation of the eyeball around the axis corresponding to the line of sight, known as its torsional rotation. Once the 3D model (110 in FIG. 3) has been fitted to the video image, the pattern of fibrils visible in regions 117-118 (the iris), known as the "iris texture", is used to determine torsional rotations by the following procedures:
 i) The 3D model 110 is fitted to the eye region of the video image 106.
 ii) The iris texture is defined as the video image in the iris region (117-118) for each eye in each video frame.
 iii) The iris texture in each eye in each video frame is transformed by applying the inverse of the 3D model parameters of the head position to the appearance it would have if viewed from straight ahead.
 iv) In each video frame after the first one, the computed straight-ahead view of the iris regions in each frame is cross-correlated with respect to angular variations around the line of sight with the corresponding region in the previous video frame.
 v) The torsion angle of maximum cross-correlation is taken as the estimated torsional rotation angle of the iris between each successive pair of video frames.
 vi) The changes in computed rotation angle are stored in the trajectory accumulator 135 in FIG. 4 to form the trajectories of the torsional rotation angles of each eye.
 vii) The torsional trajectories are then tracked and subjected to the same forms of assessment of oculomotor dynamics as for the vector rotations of the line of sight.

In accordance with one aspect, the eye-tracking system is based on a Bayesian 3D model of the typical configurations of the eyeballs, irises, pupils, axis geometries, and eyelids of the two eyes. In particular, the Bayesian 3D model incorporates known values for the average diameters of the eyeballs and irises, of the average separation between the two eyeballs, of the average angle between the visual axis of the gaze and the pupillary axis (known in the ophthalmic literature as "angle kappa"), and of the average angular widths of the eyelid apertures.

The Bayesian 3D model of the configurations of the eyeballs and eyelids (110 in FIGS. 3 and 4) is fitted to the corresponding features visible in the video frame image by adjusting the free parameters of the 3D model 110, including the relative positions, sizes and ellipticities of the iris boundaries and pupil apertures of the two eyes based on the gaze angles of the eyes, and the openness of the eyelids. The particular feature that is the focus of the eye-tracking principle in the present system is the regions of the sclera (121 and 122 in FIG. 3), or the "white of the eye" defined by the intersection of the outer boundary of the iris with the inner boundaries of the eyelids. In the normal centered position, each eye image exhibits two such regions of quasi-triangular form, one on the nasal side and one on the temporal side in each eye. When the gaze is in extreme leftward or rightward positions, one of these regions may disappear, leaving only the other one. When the eyelids are wide open, the two regions on either side of the iris may coalesce into a single continuous scleral region connecting above or below the iris. In all cases, the free parameters defining the 3D shape of this region in the 3D model 110 is optimized to fit the image information as to the shape of the sclera in each image frame. We are not aware of any previous use of the shape of the visible scleral region as the basis for an eye-tracking system.

By quantifying these free parameters in each video frame, and cumulating their changes over time, the system provides an assessment of the gaze angles of both eyes from widely available consumer devices incorporating a camera without the use of any specialized eye-tracking equipment. The use of the Bayesian parameter assumptions in the 3D model enables the operation of the eye-tracking system to operate directly from a video of the face without the use of a calibration step. The resulting gaze angle estimates from each video frame may then be fed to a computational program that derives the kinetic and dynamic parameters of the gaze trajectories over time, and fits of model functions for these gaze trajectories to characterize the degree of normality and deviation from normality of the oculomotor parameters of the two eyes.

Accordingly the reader will see that, based on various aspects and ramifications, one general advantage of the gaze trajectory measurement system is to assess the movements of the eyes, together with the variations in pupil diameters and the accommodative status of the lenses, from video images of a person's face without the need for any calibration procedures. These advantages are achieved by means of the application of the Bayesian 3D model of the geometry of the two eyes to assessing the positions of the visible features of the eyeball and eyelids. The various embodiments probe these oculomotor functions in different ways and to different extents. Other embodiments are similar to those described but track different features of eyes or use different forms of light energy to form the video images.

While the above description contains many specificities, these should not be construed as limitations on the scope, but as exemplifications of the presently preferred embodiments thereof. The detailed description is directed to certain implementations for the purposes of describing the innovative aspects of this disclosure. However, a person having ordinary skill in the art will readily recognize that the teachings herein can be applied in a multitude of different ways. The described implementations may be provided in any device, apparatus, or system that is configured with a front-facing camera that provides a high-resolution image of the users eyes. More particularly, it is contemplated that the described implementations may be included in or associated with a variety of electronic devices such as, but not limited to, television receivers, hand-held or portable computers, netbooks, notebooks, smartphones, tablet computers, television monitors, flat panel displays, computer monitors, video projectors, electronic reading devices (e.g., e-readers), gaming consoles, virtual reality devices, wearable electronics, and inbuilt architectural displays. Thus, the teachings are not intended to be limited to the implementations depicted solely in the figures, but instead have wide applicability in diverse implementations as will be readily apparent to one having ordinary skill in the art.

Many other ramifications and variations are possible within the teachings. One example is the use of the eye-tracking capability in a consumer device incorporating a camera in conjunction with computing capabilities configured for interactive control of software, as in a computer game, or control of hardware, as in a robot.

A second example the use of the system to measure deficits in the parameters of saccadic or vergence eye movement, such as amplitude, onset latency, duration, and maximum velocity of eye movements in response to predetermined visual target movements.

A third example is the use of the use of the system for the diagnosis of ophthalmic disorders such as strabismus, nystagmus or ocular instabilities. These ophthalmic disorders are typically diagnosed and monitored by a physician observing the rotational angles and movements of the eyes during a clinical examination, and are often documented by videotaping the eyes during such procedures. A 3D model with a condition of strabismus is illustrated in FIG. 6, in which the right eye (the eye on the left in the figure) is shown as deviating inward from the straight-ahead position illustrated in FIG. 3. In this way, the system can be used to quantify the rotational angles and movement dynamics of the eyes over time from the videotape records of such examinations, both providing objective documentation of subjective observations in the examination, and providing quantitative data for further scientific and clinical analysis of the detailed behavior of the eyes in such ophthalmological disorders.

A fourth example of the use of the system is for assessing and comparing the oculomotor skills of high-performing individuals participating in sports teams and or acting as emergency responders. In such applications, the movements of the eyes can be videotaped while undergoing a sequence of standardized movements specified in a printed visual display card or an electronically controlled visual display screen. The videotape analysis of the present system would then provide quantification of the individual's oculomotor performance and compare it with the standardized values set by a previous sample from the individual undergoing the standardized sequence of movements. Such a comparison provides the means to diagnose deficits in eye movement behavior resulting from stressful events encountered by these individuals.

A final example is the use of the system for scientific studies of the normal capabilities of the oculomotor control pathways in humans and other laboratory species, about which a great deal remains to be studied. In this case the experimenter would employ the system to analyze oculomotor dynamics under for little studied aspects of oculomotor behavior, such as fixating at different distances or tracking objects moving in 3D space.

Thus the full scope of the various embodiments and aspects should be determined by the appended claims and their legal equivalents and not limited by the examples given.

The invention claimed is:

1. A method for tracking 3D positions and angles of gaze of the eyes in space from facial information in video or other image sequences of the eye region of the face of an individual, whereby said information comprises a 2D projection each of a plurality of 3D configurations of one or more of the following facial features:
   i) an eyeball having a spherical radius and a 3D position,
   ii) an upper eyelid having an angle of closure,
   iii) a lower eyelid having an angle of closure,
   iv) an iris having a circular radius and center with a two-parameter location relative to the center of said eyeball defining the angle of gaze,
   v) a pupil having a circular radius,
   vi) a scleral region bounded by an iris, an upper eyelid and a lower eyelid;
said method comprising:
   obtaining a video image of the eyes of a subject illuminated by ambient light, said video image comprising an array of image pixels, each of said pixels having an image pixel trichromatic value,
   storing said video image in a electronic storage buffer,
   providing a standard 3D geometric model of said facial features, said 3D geometric model incorporating a plurality of adjustable parameters of said 3D configurations of said facial features, including said 3D locations, angles of gaze, and pupil radii,
   deriving a projected 2D view of said 3D geometric model of said facial features, said 2D view comprised of model pixels;
   defining a plurality of zones of said projected 2D view, each corresponding to one of said facial features, each of said zones containing a respective plurality of model pixels, each of said model pixels having a model pixel trichromatic value,
   determining the average trichromatic value of a plurality of said model pixels in each of said zones,
   determining the deviation of the image pixel trichromatic value of each of said plurality of said image pixels from said average trichromatic value of said plurality of said model pixels in each of said zones to determine a trichromatic pixel error value for each of said image pixels,
   combining said trichromatic pixel error values across said plurality of said zones to calculate a combined error value over a plurality of said image zones constrained by said 3D geometric model,
   varying said adjustable parameters of said geometric 3D model and repeating the steps of deriving a 2D view, determining the deviation of the image pixel trichromatic values and determining the trichromatic pixel error values and calculating the combined error values over a plurality of the image zones in an iterative loop until said combined error value across said plurality of image zones converges to a minimum value,
   storing in a trajectory accumulator said values of said adjustable parameters, including one or more of said 3D positions, angles of gaze, eyelid angles of closure and pupil sizes of said eyes, under conditions providing said minimum values of said combined error values, to form trajectories of said adjustable parameters over time,
whereby trajectories of said eyeball positions, angles of gaze, eyelid angles of closure, and pupil radii are tracked over time, where said tracking is done without calibration and without the use of any specialized equipment except widely available consumer devices incorporating a camera selected from the group including:
   i) video cameras,
   ii) television monitors
   iii) smartphones
   iv) tablet computers
   v) laptop computers
   vi) desktop computers
   vii) gaming consoles
   viii) virtual reality devices
   ix) wearable electronics
   x) inbuilt architectural displays.

2. The method of claim 1 wherein said image sequences of said eye region of the face are selected from the group consisting of:
   i) single frame images from a camera,
   ii) film sequences from a film camera converted to digital format,
   iii) digital image sequences from a visible light camera or other image acquisition device
   iv) digital image sequences digital image sequences acquired through infrared light or other regions of the electromagnetic spectrum.

3. The method of claim 1 further including the step of analyzing said trajectories stored in said trajectory accumulator to derive kinetic parameters of their dynamic behavior or to fit said trajectories by dynamic model functions that characterize their dynamic behavior as a function of time.

4. The system of claim 1 wherein a plurality of 3D positions of said eyes are further derived from images of a user of a consumer device incorporating a viewing screen and a video camera, said video camera being attached in a fixed relationship to said consumer device, said viewing screen containing predetermined information relevant to said user, and said 3D positions of said eyes providing an estimate of a target of attention of said user on said viewing screen for use in interactive control of screen content.

5. The system of claim 1 wherein a plurality of 3D positions of said eyes are further derived from a camera in conjunction with computing capabilities on a consumer device, and used for interactive control of software and/or hardware.

6. The method of claim 1 wherein said parameter values of said iris radii and said imaginary line joining said centers of the two eyeballs are stored in said storage buffer, said parameter values being used to verify an absolute position of said face estimated from said geometric 3D model of said relative 3D configuration of the two eyes, said parameter values of said iris sizes and said distance between the pupils further being obtained from one or more of the following sources:
   i) direct measurement when the eyes are in parallel gaze,
   ii) published data on the variation with age of said parameters,
   iii) input from said geometric 3D model values measured by said system when the participant's gaze is fixated on a plurality of known fixation locations on said viewing screen of said consumer device.

7. The method of claim 1 wherein torsional rotation of an eye around its optic axis is estimated from a plurality of said image pixel trichromatic values for pixels lying within said zones of scleral and iris features of an eye.

8. The method of claim 1 wherein the distributions of said image pixel trichromatic values of said pixels within said zones of scleral and iris features are trimmed to remove outlier values in order to minimize distortions of said adjustable parameters from said zones due to specular glint reflections of incident light sources.

9. The method of claim 1 wherein said projected 2D view of said 3D geometric model of said eye region further incorporates a calculation of a plurality of gradations in illumination based on the configuration of said 3D model of said facial features relative to sources of illumination.

10. The method of claim 1 wherein changes in the 3D position of said eye region of said face in space are estimated from parameters defining said geometric 3D model of the two eyes.

11. A process for tracking 3D positions and angles of gaze of the eyes in space from facial information in video or other image sequences of said eye region of the face of an individual, whereby said information comprises a 2D projection of each of a plurality of 3D configurations of one or more of the following facial features:
  i) an eyeball having a spherical radius and a 3D position,
  ii) an upper eyelid having an angle of closure,
  iii) a lower eyelid having an angle of closure,
  iv) an iris having a circular radius and center with a two-parameter location relative to the center of said eyeball defining the angle of gaze,
  v) a pupil having a circular radius,
  vi) a scleral region bounded by an iris, an upper eyelid and a lower eyelid,
said process comprising the steps of:
  obtaining a video image of the eyes of a subject, said video image comprising an array of image pixels, each of said pixels having an image pixel trichromatic value,
  storing said video image in a storage buffer,
  providing a standard 3D geometric model of said facial features, said 3D geometric model incorporating a plurality of adjustable parameters of said 3D configurations of said facial features, including said 3D locations, angles of gaze, and pupil radii,
  deriving a projected 2D view of said 3D geometric model of said facial features, said 2D view comprised of model pixels;
  defining a plurality of zones of said projected 2D view, each corresponding to one of said facial features, each of said zones containing a respective plurality of model pixels, each of said model pixels having a model pixel trichromatic value,
  determining the average trichromatic value of a plurality of said model pixels in each of said zones,
  determining the deviation of the image pixel trichromatic value of each of said plurality of said image pixels from said average trichromatic value of said plurality of said model pixels in each of said zones to determine a trichromatic pixel error value for each of said image pixels,
  combining said trichromatic pixel error values across said plurality of said zones to calculate a combined error value over a plurality of said image zones constrained by said 3D geometric model,
  analyzing histogramically the distributions of said image pixel trichromatic values of said pixels within said zones of scleral and iris features to trim and remove outlier values due to specular glint reflections of incident light sources,
  varying said adjustable parameters of said geometric 3D model and repeating the steps of deriving a 2D view, determining the deviation of the image pixel trichromatic values and determining the trichromatic pixel error values and calculating the combined error values over a plurality of the image zones in an iterative loop until said combined error value across said plurality of image zones converges to a minimum value,
  storing in a trajectory accumulator said values of said adjustable parameters, including said 3D positions, angles of gaze, eyelid angles of closure and pupil sizes of said eyes, under conditions providing said minimum values of said combined error values, to form trajectories of said adjustable parameters over time,
  whereby the trajectories of said eyeball positions, angles of gaze, eyelid angles of closure, and pupil radii, are tracked over time, where said tracking is done without calibration and without the use of any specialized equipment except widely available consumer devices incorporating a camera selected from the group including:
    i) video cameras,
    ii) television monitors,
    iii) smartphones,
    iv) tablet computers
    v) laptop computers
    vi) desktop computers
    vii) gaming consoles
    viii) virtual reality devices
    ix) wearable electronics
    x) inbuilt architectural displays.

12. The process of claim 11 wherein said image sequences of said eye region of the face are selected from the group consisting of:
  i) single frame images from a camera,
  ii) film sequences from a film camera converted to digital format,
  iii) digital image sequences from a visible light camera, or other image acquisition device
  iv) digital image sequences acquired through infrared light or other regions of the electromagnetic spectrum,
  v) digital image sequences from a virtual reality device or wearable electronics.

13. The process of claim 11 further including the process of analyzing said trajectories stored in said trajectory accumulator to derive kinetic parameters of their dynamic behavior or to fit said trajectories by dynamic model functions that characterize their dynamic behavior as a function of time.

14. The process of claim 11 wherein a plurality of 3D positions of said eyes are further derived from images of a user of a consumer device incorporating a viewing screen and a video camera, said video camera being attached in a fixed relationship to said consumer device, said viewing screen containing predetermined information relevant to said user, and said 3D positions of said eyes providing an estimate of a target of attention of said user on said viewing screen for use in interactive control of screen content.

15. The process of claim 11 wherein a plurality of 3D positions of said eyes are further derived from a camera in conjunction with computing capabilities on a consumer device, and used for interactive control of software or/and hardware.

16. The process of claim 11 further including the step of storing said parameter values of said iris radii and said imaginary line joining said centers of the two eyeballs in said storage buffer, estimating an absolute position of said face from said geometric 3D model of said relative 3D configuration of the two eyes, said parameter values of said iris sizes and said distance between the pupils further being obtained from one or more of the following sources:
  i) direct measurement when the eyes are in parallel gaze,
  ii) published data on the variation with age of said parameters,
  iii) input from said geometric 3D model values measured by said system when the participant's gaze is fixated on a plurality of known fixation locations on said computer monitor.

17. The process of claim 11 wherein torsional rotation of an eye around its optic axis is estimated from a plurality of said image trichromatic values for pixels lying within said zones of scleral and iris features of an eye.

18. The process of claim 11 wherein said projected 2D view of said 3D geometric model of said zones of scleral and iris features incorporates a calculation of a plurality of gradations in illumination based on the configuration of said 3D model of said facial features relative to sources of illumination.

19. The process of claim 11 wherein changes in 3D position of said eye region of said face are estimated from parameters defining said geometric 3D model of the two eyes.

* * * * *